(12) United States Patent
Guala

(10) Patent No.: US 6,390,120 B1
(45) Date of Patent: May 21, 2002

(54) CHECK VALVE FOR MEDICAL INFUSION LINES AND THE LIKE

(75) Inventor: Gianni Guala, Turin (IT)

(73) Assignee: Industrie Borla S.p.A., Turin (IT)

( * ) Notice: Subject to any disclaimer, the term of this patent is extended or adjusted under 35 U.S.C. 154(b) by 0 days.

(21) Appl. No.: 09/710,445

(22) Filed: Nov. 10, 2000

(30) Foreign Application Priority Data

Nov. 12, 1999 (IT) .......................... TO99A0973

(51) Int. Cl.[7] .......................... F16K 15/14; A61M 39/22
(52) U.S. Cl. .................... 137/512.15; 137/843; 604/247
(58) Field of Search ............................ 137/512.15, 843; 604/247

(56) References Cited

U.S. PATENT DOCUMENTS 3,010,477 A * 11/1961 Graham ...................... 137/860
3,601,151 A * 8/1971 Winnard ...................... 137/846
3,601,152 A * 8/1971 Kenworthy .................. 137/843
3,797,522 A * 3/1974 Carleton ...................... 137/853
3,889,710 A * 6/1975 Brost ..................... 137/512.15
4,712,583 A * 12/1987 Pelmulder et al. .......... 137/852
4,946,448 A * 8/1990 Richmond .................. 137/843
5,660,205 A * 8/1997 Epstein .................. 137/512.15
5,775,671 A * 7/1998 Cote, Sr. .................. 251/149.1
5,954,313 A * 9/1999 Ryan ........................ 251/149.1

* cited by examiner

Primary Examiner—Michael Powell Buiz
Assistant Examiner—Ramesh Krishnamurthy
(74) Attorney, Agent, or Firm—TraskBritt

(57) ABSTRACT

A check valve for medical infusion lines and the like, including a diaphragm made of elastically deformable material inserted between an upstream passageway and a downstream passageway and cooperating with an annular valve seat to keep the check valve normally closed. The annular valve seat is formed by a front surface of the first tubular element, and the diaphragm consists of the bottom wall of a cup-shaped element arranged coaxially with the upstream and downstream passageways.

47 Claims, 4 Drawing Sheets

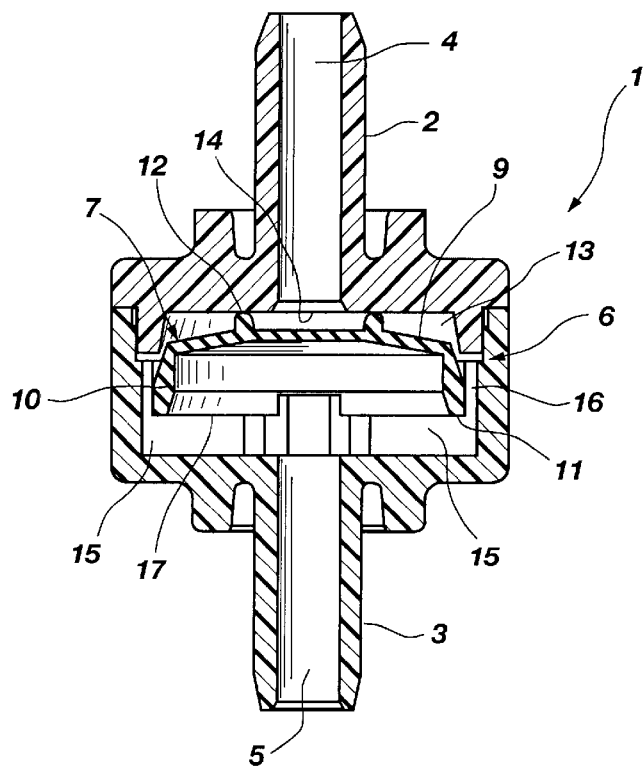
*Fig. 4*
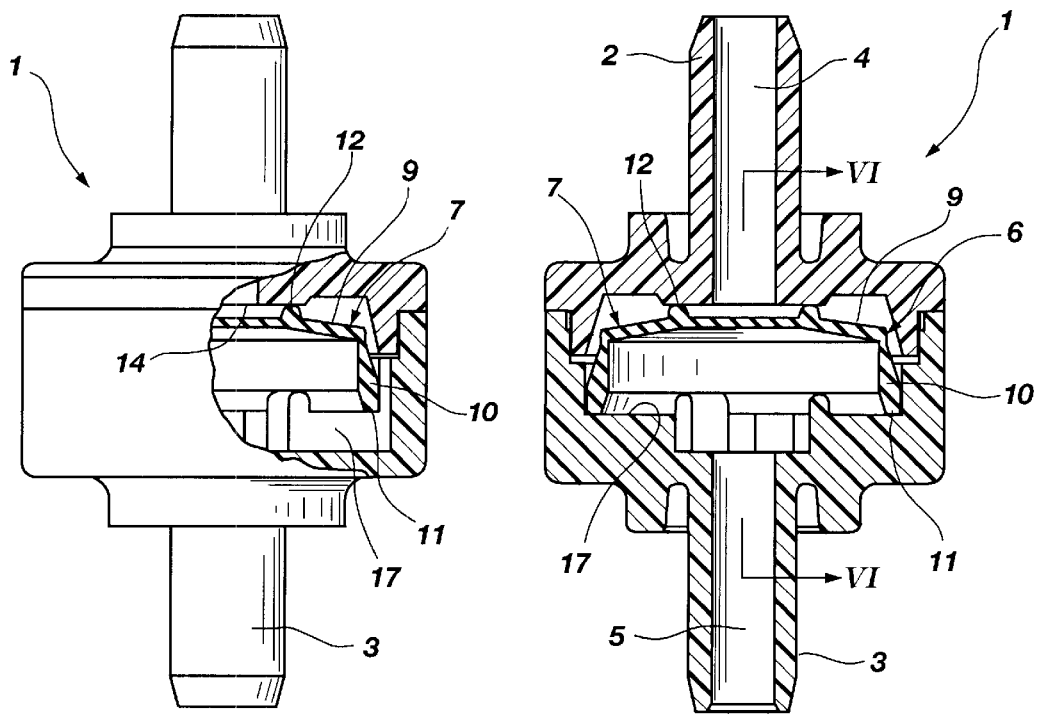
*Fig. 6*   *Fig. 5*

US 6,390,120 B1

CHECK VALVE FOR MEDICAL INFUSION LINES AND THE LIKE

BACKGROUND OF THE INVENTION

The present invention refers to check valves for medical infusion lines and the like.

Such check (or non return) valves normally comprise a first and a second tubular element that respectively define an upstream and a downstream passageway, mutually coaxial to each other and between which a diaphragm of elastically deformable material is transversely positioned, sealingly cooperating with an annular valve seat of the said first tubular element to form a fluid seal that maintains the check valve in a normally closed position, and in which a predetermined fluid pressure in the said upstream passageway causes a deflection of the diaphragm and consequent opening of the check valve.

Such check valves must meet a series of critical requirements: in the first place, they must normally be closed and must only open, continuously or intermittently, when the pressure in the upstream passageway is higher than a predetermined threshold, normally of small entity e.g. 0.005–0.02 bar. The check valve must also be capable of preventing any reflux from the downstream passageway to the upstream passageway with utmost security, i.e. it must be capable of rapidly closing itself in cases where a minimal overpressure enters the downstream passageway.

Another requirement of the check valves used in the medical applications in question consists in simple and low-cost design, in connection both with manufacturing and assembling of the check valve.

SUMMARY OF THE INVENTION

The object of the present invention is to provide a check valve of the above-referenced type wholly fulfilling the aforesaid requirements.

A further object of the present invention is to provide a check valve of the above-referenced type which is simply to adjust, upon manufacturing thereof, as a function of the user's need.

According to the invention this object is achieved essentially by the fact that the the annular valve seat is defined by a front surface of the first tubular element and the diaphragm consists of the bottom wall of a cup-shaped element coxial with said upstream and downstream passageways, said bottom wall being normally urged into seal contact against said annular valve seat under an axial thrust provided by the lateral wall of said cup-shaped element; deflexion of said bottom wall of said cup-shaped element produced in use by said predetermined fluid pressure causing axial separation thereof relative to said annular valve seat.

By virtue of this solution, in operation opening of the check valve takes place promptly even if the diaphragm constituted by the dome portion of the cup-shaped element is subjected to a relative high axial pre-load so as to ensure the maximum degree of closing safety and reliability. Moreover, in the open condition of the valve any increase of the fluid flow rate will result into a proportionally greater deformation of the bottom wall of the cup-shaped element and, therefore, into a proportionally greater distance of the dome portion relative to the valve seat.

BRIEF DESCRIPTION OF THE DRAWINGS

Further characteristics and advantages of the invention will be revealed during the detailed description that follows with reference to the enclosed drawings, which are supplied purely as a non-limitative example, wherein:

FIG. 4 shows, in a reduced scale, a first variant of FIG. 1, FIG. 5 shows, in a reduced scale, a second variant of FIG. 1, FIG. 6 is a sectioned view along line VI—VI of FIG. 5.

DETAILED DESCRIPTION OF THE INVENTION

Figures 1, 3:
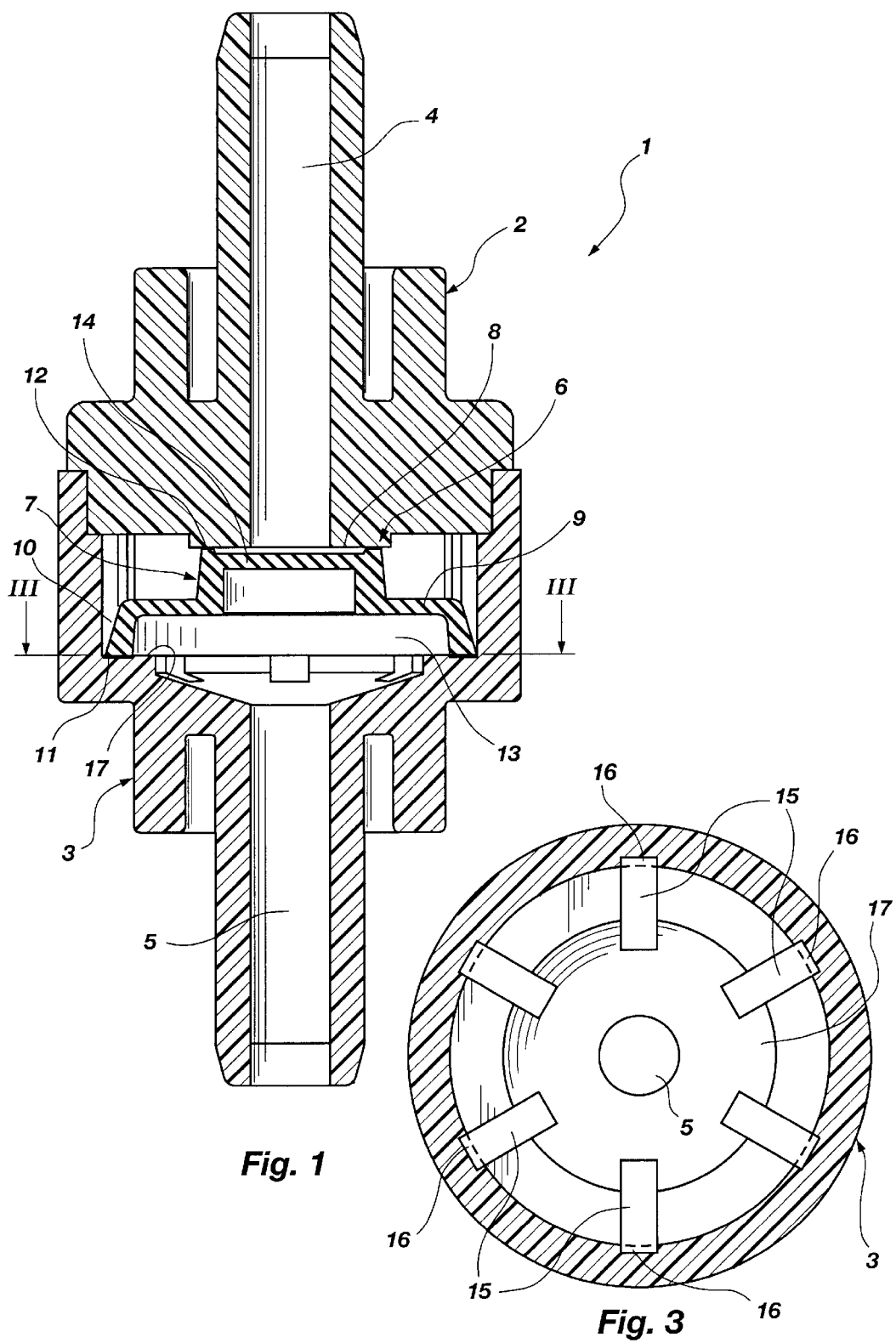
FIG. 1 is a schematic, axially sectioned view showing an axial fitting for medical infusion lines, incorporating a check valve according to the invention.
FIG. 3 is a cross section along line III—III of FIG. 1.
Figure 2:
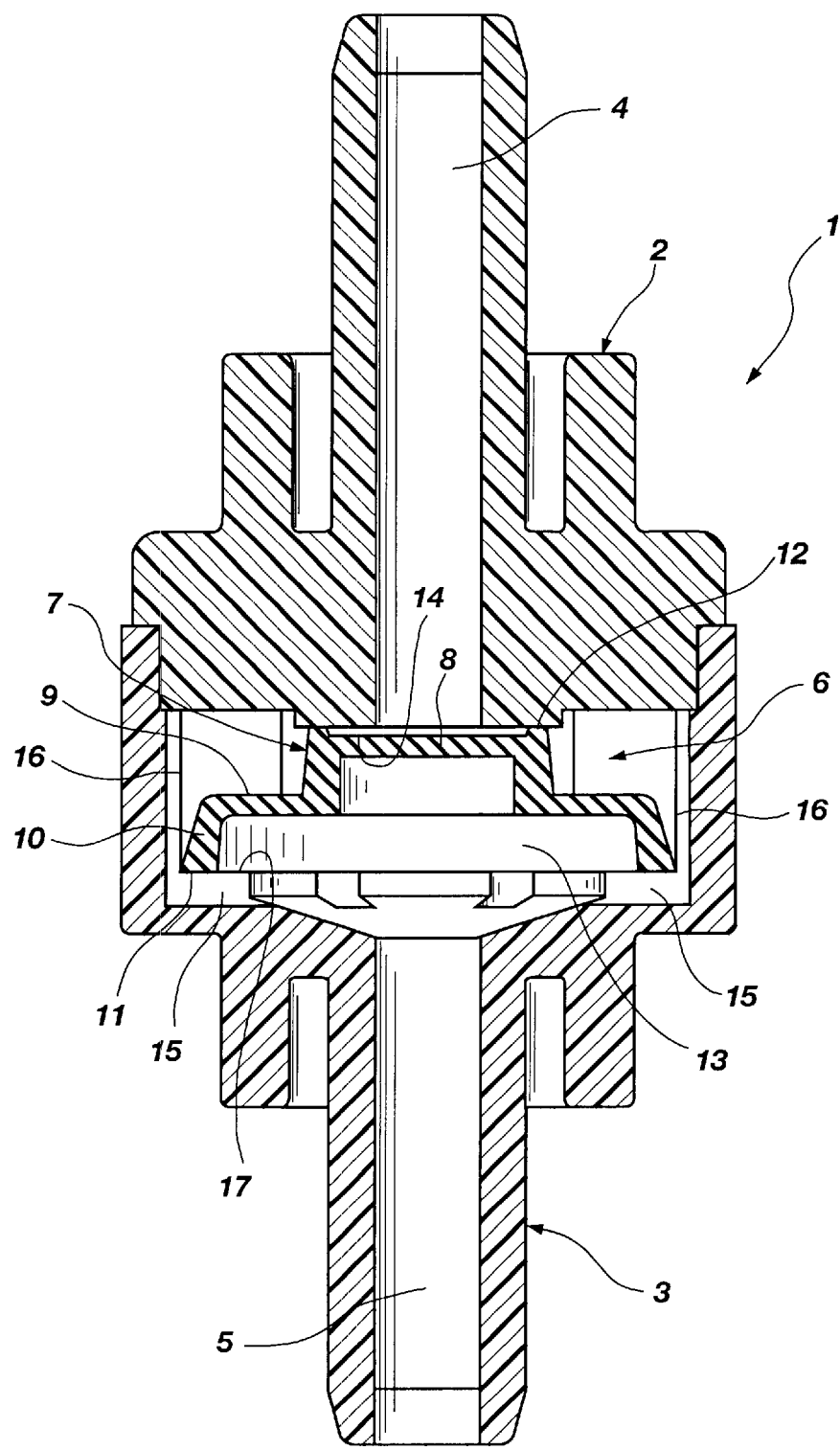
FIG. 2 is a sectioned view same as FIG. 1 but rotated of 90°.

Referring initially to FIGS. 1–3, reference numeral 1 generally designates an axial fitting for tube-to-tube connection in medical infusion lines and similar. It should be immediately noted that it could also be set up for Luer-tube, tube-Luer or Luer-Luer connections.

The fitting comprises, in a way generally known per se, a first tubular connector 2 and a second tubular connector 3 both normally made of a relatively rigid plastic material, such as polycarbonate, acrylic polymers, ABS and the like, and are coaxially joined together in a permanent way, for instance by ultrasound welding or bonding or equivalent systems.

The first and the second tubular connectors 2, 3 define an upstream passageway, or inlet passageway 4, and a downstream passageway, or outlet passageway 5, respectively, which are designed to be connected to respective tubing sections of the medical line.

A check valve, generically indicated as 6 and specifically embodying the present invention, is arranged between the upstream passageway 4 and the downstream passageway 5.

The check valve 6 essentially comprises an elastic obturator consisting of a dome portion 8 projecting axially from the central part of the bottom wall 9 of a reversed cup-shaped element 7 which, in FIGS. 1 and 2, is depicted in a condition corresponding to the closed position of the valve.

The cup element 7 comprises a shell lateral wall 10 having a cylindrical design, more suitably with a conical surface diverging towards the side opposite to the dome portion 8.

The cup-shaped element 7 is normally made in one piece of soft elastomeric material, particularly liquid silicone or thermoplastic rubber, that is injection moulded using a central injection point.

The cup-shaped element 7 can be of even thickness or, more suitably, can have a variable thickness namely greater in correspondence of the dome portion 8, smaller in correspondence of the annular bottom wall 9 and the again greater in correspondence of the lateral wall 10. Actually, the thickness of the side wall 10 may be more conveniently greater towards its free edge 11.

The dome portion 8 of the cup-shaped element is preferably flat, but may also formed at its outer circumferential edge with an annular rib defining a sealing lip 12.

The cup-shaped element 7 is fitted within a chamber 13 defined between the first tubular member 2 and the second tubular member 3, coaxially therewith. The chamber 13 is delimited at one side by a planar radial front wall 14 of the first tubular member 2, which defines in correspondence of the axially inner end of the inlet passageway 4 an annular valve seat with which the dome portion 8 (or the sealing lip 12 thereof) of the cup-shaped element 7 is cooperating.

On the other side, the chamber 13 is delimited by a channelled surface 17 coaxial to the outlet passageway 5, formed by a halo of radial channels 15 communicating with the outlet passageway 5. The radially outer end of each radial channel 15 merges into a respective axial channels 16 formed in the wall of the second tubular element 3 that laterally delimits the chamber 13.

As already mentioned, the cup-shaped element 7 is coaxially housed inside the chamber 13 with its dome portion 8 facing the inlet passageway 4 like a transversal diaphragm, and with its side wall 10 facing the axial channels 15. The free edge 11 of the lateral wall 10 rest upon the channelled surface 17 of the second tubular element 3.

The dome portion 8 (or the annular lip 12 thereof) is bearing against the annular valve seat 14 as shown iofn FIGS. 1 and 2, whereby the valve is normally closed. The arrangement is such that in the closed condition the cup-shaped element 7 is subjected to a predetermined axial preloading: in this way the wall of the dome portion (or the annular lip 12 thereof) is urged into sealing contact against the annular valve seat 14, under the axial thrust applied by the side wall 10, through the annular bottom wall 9. As pointed out, this condition corresponds to the normally closed position of the check valve 6 according to the invention, in which flow from the upstream passageway 4 to the downstream passageway 5 is prevented in an effective and safe manner.

Whenever an overpressure exceeding a predetermined threshold, for instance in the range of 0.005–0.02 bar, develops in the upstream passageway 4, the anti-siphon check valve 6 automatically and promptly switches from the closed state to the open state, due to deflexion of the annular bottom wall 9 of the cup-shaped element 7, possibly combined with a partial, axial, elastic yielding of its side wall 10. This deflexion causes the surface of the dome portion 8 (or the annular lip 12 thereof) to move away from the annular valve seat 14. The upstream passageway 4 is thus put in connection with the downstream passageway 5 via the axial channels 16 facing the side wall 10 of the cup-shaped element 7 and the radial channels 15 located beneath the free edge 11 of the lateral wall 10.

In the open state of the valve 6, as the fluid flow increases, the annular bottom wall 9, and possibly also the dome portion 8 become proportionally more and more deformed and, as a consequence, the size of the flow path is proportionally increased.

The check valve 6 immediately returns to the closed position when the pressure balance between the upstream passageway 4 and the downstream passageway 5 is re-established, or in the case of overpressure in the downstream passageway 5, due to the annular bottom wall 9 returning to the non-deflected configuration, and the dome portion 8 consequently returning to the contact position of its surface (or the annular lip 12 thereof) against the valve seat 14.

Calibration of the check valve 6 can be effected by simply working on the elastic characteristics of the cup-shaped element 7, e.g. varying the thickness of its bottom wall 9 or using materials of different hardness, or modifying assembling preloading thereof within the chamber 13.

The dome portion 8 is not strictly necessary, and in fact the three preferred alternative embodiments which shall be disclosed herebelow with reference to FIGS. 5 through 8 (wherein parts which are identical or similar to those already disclosed are indicated by the same reference numerals) havo no such dome portion. In these alternative embodiments the bottom wall 9 of the cup element 7 itself defines the diaphragm normally urged into seal contact against said annular valve seat 14 under the axial thrust provided by the lateral wall 10.

In all three alternative embodiments the side wall 10 of the cup-shaped element 7 has a cylindrical or conical surface diverging towards said channelled surface 17 and an increasing thickness from the bottom wall 9 towards its free edge 11. Moreover, in all three alternative embodiments the sealing lip 12 facing towards the valve seat 14 is provided at a distance from the lateral wall 10.

In the embodiment shown in FIG. 4 the bottom wall 9 is slightly convex towards the valve seat 14, and the thickness of the area of the bottom wall 9 corresponding to the sealing lip 12 is reduced. The front surface defining the annular valve seat 14 is oriented with an angle different than 90° relative to the axis of said first tubular element 2. For instance, the angle between the plane of the front surface 14 and the general plane of the channelled surface 17 of the second tubular element 3 may be comprised between 1° and 10°.

In the embodiment of FIGS. 5 and 6 the bottom wall 9 is also slightly convex towards the valve seat 14, b while beeng provided of a substantially even thickness. The front surface defining the annular valve seat 14 is in this case perfectly radially oriented, i.e. is perpendicular to the axis of the firts tubular element 2.

Figure 7:
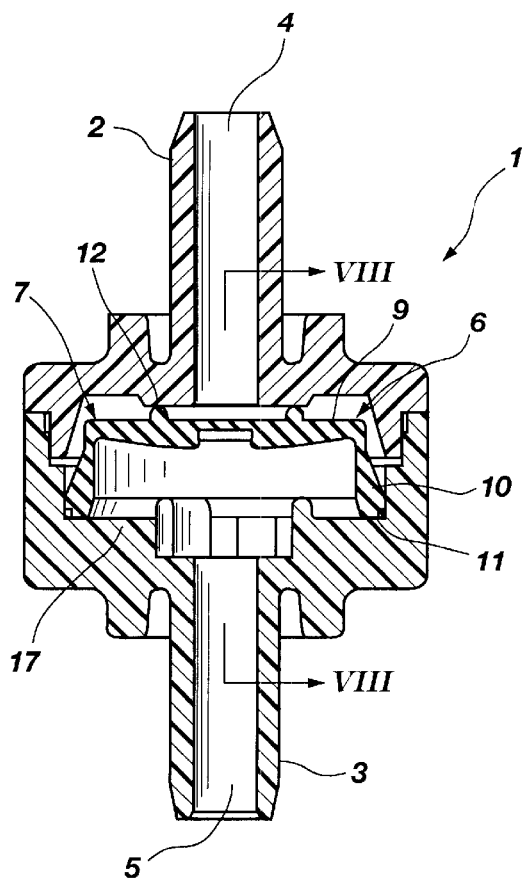
FIG. 7 shows, in a reduced scale, a third variant of FIG. 1.
Figure 8:
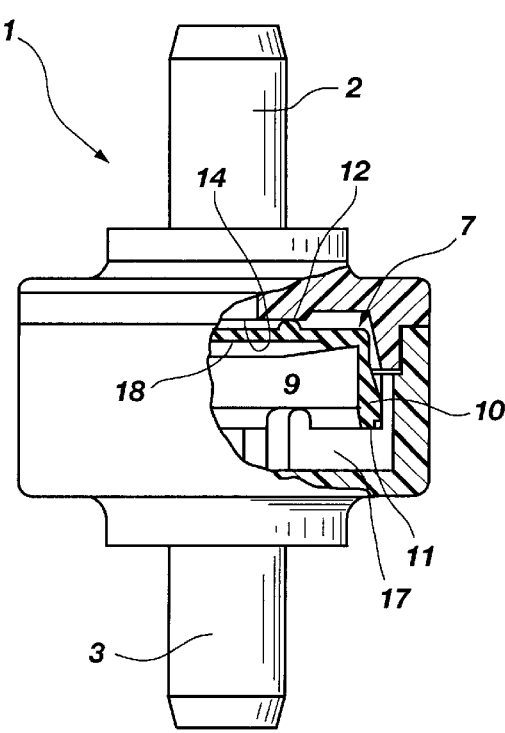
FIG. 8 is a sectioned view along line VIII—VIII of FIG. 7.

Lastly, in the embodiment of FIGS. 7 and 8 the outer surface with the sealing lip 12 of the bottom wall 9 is generally planar, with an increasing thickness towards its center along a first diametral direction but with an elongated recess 18 formed in the inner surface of the bottom wall 9 along a second diametral direction perpendicular to the first diametral direction. The design of the recess 18 may be different than the one depicted in the drawings.

Naturally, the constructional details and the embodiments could be extensively changed with respect to that described and illustrated without departing from the scope of this invention, as defined in the appended claims. In addition, although the valve has been described with express reference as a check valve, it could easily be adapted for use as an anti-siphon valve.

What is claimed is:

1. A check valve for a medical infusion line, comprising:
a first and a second tubular element positioned coaxially to each other to respectively define an upstream and a downstream passageway;
a diaphragm of elastically deformable material transversely positioned between said first and second tubular elements, said diaphragm sealingly cooperating with an annular valve seat of the said first tubular element to form a fluid seal that maintains said check valve in a normally closed position, and in which a predetermined fluid pressure in the said upstream passageway causes a deflection of said diaphragm and consequent opening of said check valve, wherein:
said annular valve seat is defined by a front surface of said first tubular element, and
wherein said diaphragm includes a cup-shaped element positioned coaxially with said upstream and downstream passageways; said cup-shaped element having a lateral wall and a bottom wall, said bottom wall contacting said annular valve seat and said lateral wall having a free edge contacting said second tubular element, said cup-shaped element being disposed in axial compression between said annular valve seat and said second tubular element, said bottom wall being normally urged into a sealing contact against said annular valve seat under an axial thrust provided by said lateral wall of said cup-shaped element; a deflection of said bottom wall of said cup-shaped element being produced in use by said predetermined fluid pressure thereby causing an axial separation of said bottom wall relative to said annular valve seat.

2. A valve according to claim 1, wherein said lateral wall of said cup-shaped element has a free edge and said second tubular element has a channelled surface communicating with said downstream passageway and upon which said free edge is resting.

3. A valve according to claim 2, wherein said lateral wall of said cup-shaped element has a cylindrical surface.

4. A valve according to claim 2, wherein the said lateral wall of said cup-shaped element has a conical surface diverging towards said channelled surface.

5. A valve according to claim 2, wherein said channelled surface has a halo of radial channels, each merging into a respective axial channel formed in said second tubular element and facing said lateral wall of said cup-shaped element.

6. A valve according to claim 1, wherein said first tubular element has a longitudinal axis and said front surface defining said annular valve seat is oriented perpendicularly to said axis.

7. A valve according to claim 1, wherein said first tubular element has a longitudinal axis and said front surface defining said annular valve seat is oriented with an angle different than 90° relative to said axis.

8. A valve according to claim 1, wherein said bottom wall of said cup-shaped element is formed with an annular rib defining a sealing lip facing towards said valve seat.

9. A valve according to claim 1, wherein said bottom wall of said cup-shaped element has a variable thickness.

10. A valve according to claim 9, wherein said bottom wall of said cup-shaped element has a central portion having a reduced thickness.

11. A valve according to claim 10, wherein said central portion of said bottom wall of said cup-shaped element is formed with a recess.

12. A valve according to claim 11, wherein said recess is diametrally oriented.

13. A valve according to claim 1, wherein said bottom wall of said cup-shaped element is slightly convex towards said valve seat.

14. A valve according to claim 2, wherein said lateral wall of said cup-shaped element has an increasing thickness from said bottom wall towards said free edge.

15. A valve according to claim 1, wherein said bottom wall of said cup-shaped element has an axially projecting dome portion.

16. A valve according to claim 1, wherein said cup-shaped element is formed from a single piece of soft, elastomeric material, namely liquid silicone that is injection molded using a central injection point.

17. A valve according to claim 1, wherein said first and second tubular elements are set up for tube-tube, Luer-tube, tube-Luer or Luer-Luer connections on said medical infusion line.

18. A check valve for a medical infusion line, comprising:
a first and a second tubular element positioned coaxially to each other to respectively define an upstream and a downstream passageway;
a diaphragm of elastically deformable material transversely positioned between said first and second tubular elements, said diaphragm sealingly cooperating with an annular valve seat of the said first tubular element to form a fluid seal that maintains said check valve in a normally closed position, and in which a predetermined fluid pressure in the said upstream passageway causes a deflection of said diaphragm and consequent opening of said check valve, wherein:
said annular valve seat is defined by a front surface of said first tubular element, and
wherein said diaphragm includes a cup-shaped element positioned coaxially with said upstream and downstream passageways; said cup-shaped element having a lateral wall and a bottom wall, said bottom wall being normally urged into a sealing contact against said annular valve seat under an axial thrust provided by said lateral wall of said cup-shaped element; a deflection of said bottom wall of said cup-shaped element being produced in use by said predetermined fluid pressure thereby causing an axial separation of said bottom wall relative to said annular valve seat, wherein said lateral wall of said cup-shaped element has a free edge and said second tubular element has a channelled surface communicating with said downstream passageway and upon which said free edge is resting.

19. A valve according to claim 18, wherein said lateral wall of said cup-shaped element has a cylindrical surface.

20. A valve according to claim 18, wherein the said lateral wall of said cup-shaped element has a conical surface diverging towards said channelled surface.

21. A valve according to claim 18, wherein said channelled surface has a halo of radial channels, each merging into a respective axial channel formed in said second tubular element and facing said lateral wall of said cup-shaped element.

22. A valve according to claim 18, wherein said first tubular element has a longitudinal axis and said front surface defining said annular valve seat is oriented perpendicularly to said axis.

23. A valve according to claim 18, wherein said first tubular element has a longitudinal axis and said front surface defining said annular valve seat is oriented with an angle different than 90° relative to said axis.

24. A valve according to claim 18, wherein said bottom wall of said cup-shaped element is formed with an annular rib defining a sealing lip facing towards said valve seat.

25. A valve according to claim 18, wherein said bottom wall of said cup-shaped element has a variable thickness.

26. A valve according to claim 18, wherein said lateral wall of said cup-shaped element has an increasing thickness from said bottom wall towards said free edge.

27. A valve according to claim 18, wherein said bottom wall of said cup-shaped element has an axially projecting dome portion.

28. A valve according to claim 18, wherein said cup-shaped element is formed from a single piece of soft, elastomeric material, namely liquid silicone that is injection molded using a central injection point.

29. A valve according to claim 18, wherein said first and second tubular elements are set up for tube-tube, Luer-tube, tube-Luer or Luer-Luer connections on said medical infusion line.

30. A check valve for a medical infusion line, comprising:
a first and a second tubular element positioned coaxially to each other to respectively define an upstream and a downstream passageway;
a diaphragm of elastically deformable material transversely positioned between said first and second tubular elements, said diaphragm sealingly cooperating with an annular valve seat of the said first tubular element to form a fluid seal that maintains said check valve in a normally closed position, and in which a predetermined fluid pressure in the said upstream passageway causes a deflection of said diaphragm and consequent opening of said check valve, wherein:
said annular valve seat is defined by a front surface of said first tubular element, and
wherein said diaphragm includes a cup-shaped element positioned coaxially with said upstream and downstream passageways; said cup-shaped element having a lateral wall and a bottom wall, said bottom wall being normally urged into a sealing contact against said annular valve seat under an axial thrust provided by said lateral wall of said cup-shaped element; a deflection of said bottom wall of said cup-shaped element being produced in use by said predetermined fluid pressure thereby causing an axial separation of said bottom wall relative to said annular valve seat, wherein said bottom wall of said cup-shaped element has a variable thickness and a central portion having a reduced thickness.

31. A valve according to claim 30, wherein said central portion of said bottom wall of said cup-shaped element is formed with a recess.

32. A valve according to claim 31, wherein said recess is diametrally oriented.

33. A valve according to claim 30, wherein said first tubular element has a longitudinal axis and said front surface defining said annular valve seat is oriented perpendicularly to said axis.

34. A valve according to claim 30, wherein said first tubular element has a longitudinal axis and said front surface defining said annular valve seat is oriented with an angle different than 90° relative to said axis.

35. A valve according to claim 30, wherein said bottom wall of said cup-shaped element is formed with an annular rib defining a sealing lip facing towards said valve seat.

36. A valve according to claim 30, wherein said bottom wall of said cup-shaped element has a variable thickness.

37. A valve according to claim 30, wherein said bottom wall of said cup-shaped element has an axially projecting dome portion.

38. A valve according to claim 30, wherein said cup-shaped element is formed from a single piece of soft, elastomeric material, namely liquid silicone that is injection molded using a central injection point.

39. A valve according to claim 30, wherein said first and second tubular elements are set up for tube-tube, Luer-tube, tube-Luer or Luer-Luer connections on said medical infusion line.

40. A check valve for a medical infusion line, comprising:
a first and a second tubular element positioned coaxially to each other to respectively define an upstream and a downstream passageway;
a diaphragm of elastically deformable material transversely positioned between said first and second tubular elements, said diaphragm sealingly cooperating with an annular valve seat of the said first tubular element to form a fluid seal that maintains said check valve in a normally closed position, and in which a predetermined fluid pressure in the said upstream passageway causes a deflection of said diaphragm and consequent opening of said check valve, wherein:
said annular valve seat is defined by a front surface of said first tubular element, and
wherein said diaphragm includes a cup-shaped element positioned coaxially with said upstream and downstream passageways; said cup-shaped element having a lateral wall and a bottom wall, said bottom wall being normally urged into a sealing contact against said annular valve seat under an axial thrust provided by said lateral wall of said cup-shaped element; a deflection of said bottom wall of said cup-shaped element being produced in use by said predetermined fluid pressure thereby causing an axial separation of said bottom wall relative to said annular valve seat, wherein said bottom wall of said cup-shaped element is slightly convex towards said valve seat.

41. A valve according to claim 40, wherein said first tubular element has a longitudinal axis and said front surface defining said annular valve seat is oriented perpendicularly to said axis.

42. A valve according to claim 40, wherein said first tubular element has a longitudinal axis and said front surface defining said annular valve seat is oriented with an angle different than 90° relative to said axis.

43. A valve according to claim 40, wherein said bottom wall of said cup-shaped element is formed with an annular rib defining a sealing lip facing towards said valve seat.

44. A valve according to claim 40, wherein said bottom wall of said cup-shaped element has a variable thickness.

45. A valve according to claim 40, wherein said bottom wall of said cup-shaped element has an axially projecting dome portion.

46. A valve according to claim 40, wherein said cup-shaped element is formed from a single piece of soft, elastomeric material, namely liquid silicone that is injection molded using a central injection point.

47. A valve according to claim 40, wherein said first and second tubular elements are set up for tube-tube, Luer-tube, tube-Luer or Luer-Luer connections on said medical infusion line.

* * * * *